United States Patent [19]
Welle et al.

[11] 4,086,361
[45] Apr. 25, 1978

[54] AMINOETHYL OXIMES HAVING ANTI-DEPRESSIVE ACTIVITY

[75] Inventors: Hendricus Bernardus Antonius Welle, Utrecht; Volkert Claassen, Weesp, both of Netherlands

[73] Assignee: U.S. Philips Corporation, New York, N.Y.

[21] Appl. No.: 668,479

[22] Filed: Mar. 19, 1976

[30] Foreign Application Priority Data

Mar. 20, 1975 Netherlands .................... 7503312

[51] Int. Cl.² .................. A61K 31/15; A61K 31/275; C07C 121/78; C07C 131/00
[52] U.S. Cl. ............................. 424/304; 260/465 E; 260/501.17; 260/566 AE; 424/316; 424/327
[58] Field of Search ............... 260/566 AE, 465 E; 424/327, 304

[56] References Cited
U.S. PATENT DOCUMENTS 3,692,835  9/1972  Van Dijk et al. .................... 260/566

Primary Examiner—Dolph H. Torrence
Attorney, Agent, or Firm—Frank R. Trifari; Norman N. Spain

[57] ABSTRACT

The compounds of the formula

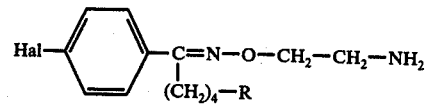

where Hal is Br or Cl and R is ethoxy, methoxymethyl, ethoxymethyl, cyano, methoxyethoxy or cyanomethyl when Hal is Cl and is cyano, methoxy or methoxyethoxy when Hal is Br and their salts have a strong antidepressive activity resulting in a powerful potentiation of noradrenalin and in a strong serotonin potentiation. Monoamino oxidase inhibition does not provide a basis for the antidepressive activity of these compounds. The compounds are free from noxious side effects to a considerable extent, for example, broncho-constriction and stomach ulceration.

13 Claims, No Drawings

AMINOETHYL OXIMES HAVING ANTI-DEPRESSIVE ACTIVITY

The following table shows properties of the compounds of formula I and of the related known compounds.

| form. I | | | noradrenalin potentiation | serotonin potentiation | MAO inhibition | Stomach ulceration | broncho constriction |
|---|---|---|---|---|---|---|---|
| Hal | R | | | | | | |
| Cl | OC$_2$H$_5$ | * | 4.3 | 36 | >215 | — | — |
| Cl | C$_2$OCH$_3$ | ** | 5.3 | 36 | >215 | — | — |
| Cl | CH$_2$OC$_2$H$_5$ | ** | 7.4 | 54 | >215 | — | — |
| Cl | OC$_2$H$_4$OCH$_3$ | * | 4.0 | 41 | >215 | — | — |
| Br | OC$_2$H$_4$OCH$_3$ | * | 6.6 | 35 | >215 | — | — |
| Cl | CN | ** | 6.8 | 20 | >215 | — | — |
| Cl | CH$_2$CN | ** | 11 | 38 | >215 | — | — |
| Br | CN | ** | 11.2 | 20 | >215 | — | — |
| Br | OCH$_3$ | * | 6.6 | 22 | >215 | — | — |
| Cl | H | ** | 5.6 | 12 | >215 | + | — |
| Cl | CH$_3$ | *** | 1.9 | 14 | >215 | + | + |
| Br | CH$_3$ | ** | 3.1 | 10 | >215 | + | — |

The invention relates to novel compounds having anti-depressive activity.

British Patent Specification No. 1,205,665 describes a large group of compounds having an antidepressive, sedative and/or anti-convulsive activity. The anti-depressive activity of the known compounds may or may not be based on monoamino oxidase inhibition.

Compounds inhibiting monoamino oxidase are particularly difficult to use. They often have serious side effects and they are often not compatible with other medicines and with nutrients.

Regulations imposed upon the sale and use of medicines become more and more stringent and these regulations cause that only those compounds are considered for administration to human beings which are substantially free from noxious side effects.

It is the object of the invention to provide novel anti-depressive agents which have no activity component based on monoamino oxidase inhibition and which in addition are substantially free from noxious side effects.

It has been found that these requirements are fulfilled by compounds represented by formula I

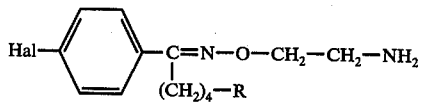

and salts thereof formed with pharmaceutically acceptable acids. In this formula, Hal is a chlorine atom or a bromine atom and R is an ethoxy-, methoxymethyl-, ethoxymethyl-, methoxyethoxy, cyano- or cyanomethyl group when Hal is a chlorine atom, and a cyano-, methoxy-, or methoxyethyoxy group when Hal is a bromine atom. The anti-depressive activity of the compounds according to the invention is expressed both in a powerful potentiation of nor-adrenalin and in a strong serotonin potentiation. However, the compounds have no monoamino oxidase (MAO) inhibiting effect.

In contrast with structurally closely related compounds which are known from the above-mentioned British Patent Specification, the compounds according to the invention surprisingly give no stomach ulceration and bronchoconstriction.

The compounds according to the invention have a very low toxicity and neurotoxicity.

The numbers in this table are ED$_{50}$ values, expressed in mg/kg. * = fumarate 1 : 1,  = hydrochloride, * = maleate 1 : 1. The above data were determined in the following tests.

The noradrenaline potentiation was determined in the tetrabenazine test. In this test a quantity of the compound to be tested was administered orally to five male albino mice. After 45 minutes the animals were injected subcutaneously with 80 mg/kg of tetrabenazine. After another 45 minutes the degree of ptosis was determined and compared with the ptosis of animals which had received tetrabenazine alone. The ED$_{50}$ was determined from the results.

The serotonin potentiation was determined in the 5-hydroxytryptophan test. For this purpose, the compounds to be tested were administered orally in a series of dosages to isolated male albino mice (5 mice per dosage) 1 hour prior to intraperitoneal administration of 150 mg/kg of dl-5-hydroxytryptophan. Thirty minutes after this threshold dosage the mice were observed individually and the following parameters were scored: stereotypical shaking of the head, spreading of the hindlegs, tremor, tendency to flee, lordosis, clonic stamping with the frontlegs. The ED$_{50}$ value was calculated from the results.

The monoamino oxidase (MAO) inhibiting effect was determined in experiments in which a quantity of the compound to be tested was administered orally to five male albino mice. One hour later the animals were injected subcutaneously with tryptamine hydrochloride in a quantity of 250 mg/kg. This quantity does not cause mortality in animals which did not receive the compound to be tested but did cause mortality in animals to which an active substance had been administered. Eighteen hours after the administration of tryptamine hydrochloride it was determined how many treated animals had died. The ED$_{50}$ was determined from the results. By means of the method by Metysova, Arzneimittelforschung 13,- 1039 (1963) it was determined whether the oral administration of 200 mg of a compound to be tested to rats causes stomach ulceration.

By means of the method by Konzett-Rossler, Arch.Exp. Path. Pharmakol. 195, 71 (1940) it was investigated whether a compound to be tested causes bronchoconstriction after intravenous administration of 3 mg. Reduction of the breathing function as a result of broncho-constriction is expressed in this method in a smaller volume of air taken in.

On the basis of their properties the compounds of formula I and their salts are particularly suitable for use in the treatment of neurotic and psychotic disturbances. In those cases the compounds may be used as a psychostimulant in the treatment of depressive patients.

The quantity in which, the frequency with which and the way in which the substances are administered may vary for each individual patient and also in accordance with the nature and the severity of the disturbances. In general, adults should be given a daily dose of from 10 to 500 mg orally. As a rule, a quantity of from 50 to 200 mg should be sufficient.

The compounds are preferably used in the form of pills, coated tablets, capsuled, powders, injection liquids and the like. The compounds may be processed to such compositions according to methods which are known per se.

The invention therefore also relates to compositions having a compound of formula I or a salt thereof as an active constituent, and to methods for preparing such compositions, for example, by mixing an active substance with or dissolving it in a solid or liquid pharmaceutical carrier material.

As examples of pharmaceutically acceptable acids with which compounds of formula I can form salts may be mentioned: hydrochloric acid, sulphuric acid, nitric acid, citric acid, fumaric acid, tartaric acid, acetic acid, benzoic acid, maleic acid, and the like.

The compounds of formula I and salts thereof formed with pharmaceutically acceptable acid may be prepared according to methods which are known for the preparation of this type of compounds and according to methods analogous thereto. The invention also relates to the preparation of the compounds.

The compounds can be obtained inter alia by reaction of a compound of formula II,

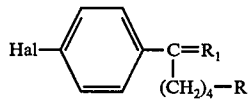

in which Hal and R have the above meanings and R is an oxygen atom, an oxime group or an alkylene-dioxy group, for example, ethylenedioxy, with a compound of formula III $H_2N - O - CH_2 - CH_2 - NH_2$ or a salt thereof. The reaction is preferably carried out in a solvent, for example, alcohols, dioxane, dimethylformamide, tetrahydrofuran, or mixtures thereof, at temperatures between room temperature and the boiling point of the mixture, preferably in the presence of an acid binder, for example pyridine.

Another method consists of a reaction between a compound of formula IV,

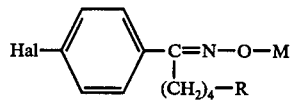

in which Hal and R have the above meanings and M is a hydrogen atom or an alkali metal atom, and a compound of formula V $R_2 - CH_2 - CH_2 - NH_2$ or a salt thereof, in which $R_2$ is a halogen atom, preferably chlorine or bromine.

The reaction is preferably carried out in an inert solvent, for example, alcohols, ethers or dimethyl-formamide. In the case in which M is a hydrogen atom, an acid binder is preferably added, for example an alkoxide. The reaction temperature as a rule is between 0° and 50° C.

The compounds can also be obtained by reacting a compound of formula VI,

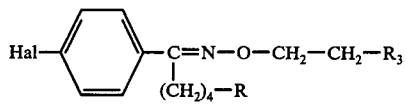

in which Hal and R have the same meanings as in formula I, and $R_3$ is a mesyloxy group or a tosyloxy group, with ammonia. The reaction is preferably carried out in a solvent, for example an alcohol, usually at temperatures between room temperature and 150° C.

The starting compounds of formula VI are prepared by converting a compound of formula IV in ethanol and in the presence of an alkoxide at temperatures up to 60° C with ethylene-oxide. The reaction product is then converted with tosylchloride or mesylchloride, into a compound of formula VI, preferably in methylenechloride as a solvent and triethylamine or pyridine as an acid binder.

Another method of preparing the compound of formula I consists of the reaction of a compound of formula VII

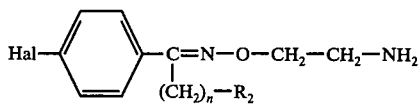

with a compound of formula VIII M—R'. In these formulae the symbols have the same meanings as in formula I, while n has the value 4 or 5, M is an alkali metal atom, R' is a methoxy-, ethoxy-, methoxy-ethoxy- or cyano group and $R_2$ is a halogen atom, preferably chlorine or bromine.

The reaction is preferably carried out in an inert solvent, for example ethanol, dimethylsulphoxide, dimethyl formamide. The reaction temperature is between 0° and 70° C.

The compounds of formula I, in which R contains an oxygen atom, may also be obtained by reacting a compound of formula IX

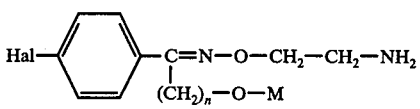

with a compound of formula $R_4$—R". In these formulae n has the value 4 or 5, Hal is a chlorine atom or a bromine atom, M is an alkali metal atom, R" is a methyl-, ethyl- or methoxyethyl group and $R_4$ is a halogen atom, for example a chlorine atom or a bromine atom or a group $(SO_4)_{\frac{1}{2}}$. The reaction is preferably carried out in an inert solvent, for example, toluene or dimethylformamide. As a rule the reaction takes place at a temperature between 0° and 80° C.

The compounds of formula I, in which R contains an oxygen atom, may also be prepared by reducing a compound of formula XI

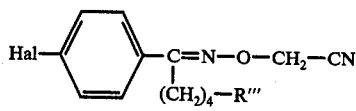

In this formula, R''' is a methoxy-, ethoxy-, methoxymethyl-, ethoxymethyl- or methoxyethoxy group.

The reaction may be carried out with a reduction agent, for example a metal hydride, for example lithium-aluminum trimethoxyhydride, in a solvent for example tetra-hydrofuran, dioxane, and the like at temperature between 0° and 25° C.

The compounds of formula I may also be obtained by converting a compound of formula XII

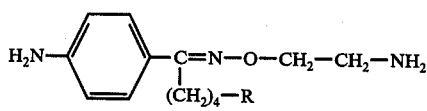

in which R has the same meaning as in formula I, with nitrous acid and hydrochloric or hydrobromic acid and converting the reaction product with copper, cuprobromide or cuprochloride.

The first step of the reaction is generally carried out in an excess of the diluted halogen acid at −10° to +5° C. The second step is carried out as a rule by the addition to copper or the copper halide at temperatures between 20° and 75° C.

The compounds of formula I may also be prepared by hydrolyzing a compound of formula XIII

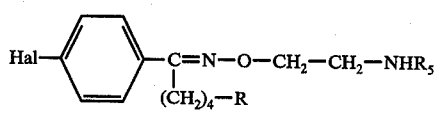

In this formula the symbols have the same meanings as in formula I, while $R_5$ is a protective group, for example, a trityl group. The reaction may be carried out in a water containing solvent under acid conditions, at temperatures between room temperature and 100° C.

The invention will be described in greater detail by means of the following examples.

EXAMPLES (1) 4'-chloro-6-methoxyprophenone O-(2-aminoethyl) oxime hydrochloride 17.5mmol (4.2 gr) of 4'-chloro-6-methoxycaprophenone, 17.5 mmol (2.6 gr) of 2-aminoxyethylamine dihydrochloride and 10 ml of pyridine were refluxed for 2 hours in 25 ml of absolute ethanol.

After evaporation the pyridine and the ethanol in vacuo, the residue was dissolved in water. 20 ml of 2 N sodium hydroxide solution were added to said solution and the whole was then extracted three times with ether. After washing with water and drying with sodium sulphate the collected ether layers were evaporated in vacuo. Thereafter, toluene was added and evaporated three times and the oil obtained was dissolved in 5 ml of absolute ethanol. To this was added an equivalent quantity of 2 N alcoholic hydrochloric acid, after which the ethanol was removed in vacuo.

The residue was crystallized from ether/petroleum ether. The melting point of the resulting compound was 71.5° - 73.5° C.

(2) 4'-chloro-6-ethoxycaprophenone O-(2-aminoethyl) oxime hydrochloride

The title compound having a melting point of 63° - 66° C was obtained in an identical manner from 4'-chloro-6-ethyoxy-caprophenone (3) 4'-chloro-5-cyanovalerophenone O-(2-aminoethyl) oxime hydrochloride The title compound having a melting point of 161° - 163° C was obtained in an identical manner from 4'-chloro-5-cyanovalerophenone.

(4) 4'-chloro-5-(2-methoxyethoxy) valerophenone O-(2-amino ethyl) oxime fumarate (1 : 1)

In an analogous manner the free base of the title compound was obtained from 4'-chloro-5-(2-methoxy-ethoxy) valerophenonene. From this the title compound was obtained with two equivalents of fumaric acid in ethanol. Melting point 134°–135.5° C.

(5) 4'-chloro-6-cyanocaprophenone O-(2-aminoethyl) oxime hydrochloride

In a manner identical to Example 1 the title compound having a melting point of 17°-108.5° C was obtained from 4'-chloro-6-cyanocaprophenone, melting point 44° - 46° C.

(6) 4'-bromo-5-(2-methoxyethoxy) valerophenone O-(2-aminoethyl) oxime fumarate (1 : 1)

In a manner identical to example 4 the title compound having a melting point of 142.5°–143.5° C was obtained from 4'-bromo-5-(2-methoxyethoxy) valerophenone, melting point 25.5° - 26.5° C.

(7) 4'-bromo-5-cyanovalerophenone O-(2-aminoethyl) oxime hydrochloride

In a manner identical to Example 1 the title compound having a melting point of 178°-179° C was obtained from 4'-bromo-5-cyanovalerophenone, melting point 47°-48° C.

(8) 4'-chloro-5-(2-methoxyethoxy)valerophenone O-(2-amino-ethyl)oxime fumarate (1 : 1)

8.0 mmol (4.3 gr) of 4'-chloro-5-(2-methoxy-ethoxy)-valerophenone 0-(2-tritylaminoethyl) oxime, melting point 61.5°– 63.5° C, were dissolved in 40 ml of 90% acetic acid. After having been left to stand at room temperature for three days, said reaction mixture was evaporated to dryness in vacuo after which the residue was dissolved in 50 ml of ether. The resulting solution was extracted with 40 ml of 0.2 n hydrochloric acid and this extract, after having been rendered alkaline with 10 ml of 2 N sodium hydroxide solution, was extracted with successively 50 and 25 ml of methylenechloride. The resulting solution was dried with sodium sulphate and evaporated in vacuo.

The residue was dissolved in 80 ml of absolute ethanol and an equimolar quantity of fumaric acid was added. The solution was then heated until a clear solution was obtained. Ether was then added, followed by crystallization at 5° C.

After sucking off and washing with ether, another crystallisation was carried out from alcohol/ether. The resulting compound had a melting point of 134°–135.5° C.

(9) 4'-chloro-6-cyanocaprophenone O-(2-aminoethyl) oxime hydrochloride.

5.0 mmol. (1.25 gr) of 4'-chloro-6-cyanocaprophenone oxime, melting point 58°–59° C, 5.2 mmol (0.60 gr) of 2-chloroethylaminehydrochloride and 0.7 gr of KOH powder were sequentially added to 12.5 ml of dimethylformamide (DMF) while stirring at 10° C.

After stirring for 2 days at room temperature, the DMF was removed in vacuo, the residue was dissolved in water and 2 N hydrochloric acid was then added until pH 3.

The remaining oxime was removed by means of ether, after which 15 ml of 2 N sodium hydroxide solution were added. Three extractions with ether were then carried out. The collected ether layers were washed with a 5% sodium bicarbonate solution and dried on sodium sulphate. After removing the ether in vacuo the residue was taken up in ethanolic hydrochloric acid. After evaporating the ethanol, the residue was crystallized from ether, melting point 107°–108.5° C.

(10) 4'-bromo-5-cyanovalerophenone O-(2-aminoethyl)oxime hydrochloride

The title compound having a melting point of 178°–179° C was obtained in an identical manner from 4'-bromo-5-cyanovalerophenone oxime, melting point 86.5°– 88° C.

(11) 4'-bromo-5-cyanovalerophenone O-(2-aminoethyl)oxime hydrochloride (a) 26 mmol. (1.15gr) of ethyleneoxide were fed (while stirring at 55° C and by means of a flow of nitrogen) into a suspension of 15.5 mol (4.3 gr) of 4'-bromo-5-cyanovalerophenone oxime, melting point 86.5°– 88° C, in 25 ml of absolute ethanol in which 0.03 g of Li had first been dissolved. Stirring was continued for an hour at 60° C. After the addition of 0.3 ml of acetic acid, the ethanol was then distilled off in vacuo and the residue was purified chromatographically by means of silica gel with $CH_2Cl_2$ as an eluent. After evaporating the solvent, the O-(2-hydroxyethyl) oxime was obtained as an oil.
(b) 2.25 ml of triethylamine were added, while stirring and at −5° C to 0° C to a solution of 11 mmol (3.6 gr) of the oxime in 60 ml of methylenechloride and 12 mmol (0.9 ml) of mesylchloride were then added dropwise in approximately 20 minutes. Stirring at 0° C was continued for thirty minutes, the mixture was then washed with ice water (4 x), with a 5% solution of sodium bicarbonate of 0° C (1 x) and with a saturated NaCl solution of 0° C (2 x), respectively. After drying on sodium sulphate at 5° C, the $CH_2Cl_2$ was distilled off in vacuo at a bath temperature of 40° to 60° C. In this manner the O-(2-mesyloxyethyl) oxime was obtained.
(c) A mixture of 8 mmol (3.2 gr) hereof with 30 mol of a methanolic solution saturated with ammonia was stirred at room temperature for 18 hours.

The ammoniacal methanol was removed in vacuo. From the residue the free base was obtained by means of chromatography over silica gel, which base was then converted into the hydrochloride by means of ethanolic hydrochloric acid. After evaporating the ethanol and dissolving the residue in ether, the title compound crystallised out. Melting point 178°–179° C.

(12) 4'-chloro-6-cyanocaprophenone O-(2-aminoethyl) oxime hydrochloride

The title compound having a melting point of 107°–108.5° C was obtained in an identical manner from 4'-chloro-6-cyanocaprophenone oxime, melting point 58°–59° C.

(13) 4'-bromo-5-(2-methoxyethoxy)-valerophenone O-(2-amino-ethyl) oxime fumarate (1 : 1)

(a) 40 mmol (12.6 gr) of 4'-bromo-5-(2-methoxyethoxy)valerophenone, melting point 25.5°–26.5° C, 143 mmol (8.9 gr) of ethyleneglycol and 2 mmol (0.35 gr) of -p-toluenesulphonic acid were dissolved in 100 ml of benzene. This solution was boiled for 48 hours in a flask having a reflux condenser and water separator.

The solution was then washed with 5% sodium bicarbonate solution (1 x) and water (1 x).

The benzene layer was then dried on sodium sulphate and evaporated in vacuo, the ethyleneketal being obtained as an oil. (b) 7 mmol (1.0 gr) of 2-aminoxyethylamine dihydrochloride and 10 ml of methanol were added to 7 mmo (2.5 gr) of its ketal and the solution was refluxed for 4 hours.

After evaporating the methanol in vacuo the residue was dissolved in water and washed twice with ether. 3 ml of 50% sodium hydroxide solution were then added and three extractions with $CH_2Cl_2$ were carried out.

This extract was washed with 5% sodium bicarbonate solution (1 x) and water (1x). The solution was then dried on sodium sulphate and the $CH_2Cl_2$ was distilled off in vacuo. The residue was converted into the fumarate (1 : 1) in a manner analogous to example 8.

After crystallization from isopropanol/acetonitrile (3 : 2) the title compound having a melting point of 142.5°–143.5° C was obtained.

(14) 4'-chloro-5-ethoxyvalerophenone O-(2-aminoethyl) oxime fumarate (1 : 1)

The title compound having a melting point of 150.5°–152° C was obtained in an identical manner from 4'-chloro-5-ethoxyvalerophenone.

(15) 4'-bromo-5-methoxyvalerophenone O-(2-aminoethyl) oxime fumarate (1 : 1)

The title compound having a melting point of 151.5°–152.5° C was obtained in an identical manner from 4'-bromo-5-methoxyvalerophenone.

(16) 4'-chloro-5-cyanovalerophenone O-(2-aminoethyl)oxime hydrochloride 10 mmol (3.3 gr) of 4',5-dichlorovalerophenone O-(2-amino ethyl)oxime hydrochloride, melting point 140°–141.5° C, were dissolved in 10 ml of dimethylsulphoxide. 25 mmol (1.2 gr) of sodium cyanide were added to said solution.

This suspension was heated at a temperature of 50° to 70° C for 3 hours and was then cooled to room temperature. The suspension was then diluted with 100 ml of 0.5 N sodium hydroxide solution and extracted three times with 40 ml of ether. This ether extract was washed with water with water one time, dried on sodium sulphate and evaporated in vacuo. The residue was purified chromatographically over silica gel with ethanol/ammonia (95 : 5) as an eluent. After evaporating the solvents, the hydrochloride was made from the resulting free base in a manner analogous to example 11c.

After a few crystallizations from ethanol/ether (1 : 3) the title compound having a melting point of 161° - 163° C was obtained.

(17) 4'-chloro-5-ethoxyvalerophenone O-(2-aminoethyl)oxime fumarate (1 : 1)

The title compound having a melting point of 150.5° - 152° C was obtained in an identical manner from 4',5-dichlorovalerophenone O-(2-aminoethyl)oxime hydrochloride, melting point 140° - 141.5° C.

(18) 4'-bromo-5-methoxyvalerophenone O-(2-aminoethyl)oxime fumarate (1 : 1)

The title compound having a melting point of 151.5° - 152.5° C was obtained in an identical manner from 4'-bromo-5-chlorovalerophenone O-(2-aminoethyl) oxime hydrochloride, melting point 141° - 142° C.

(19) 4'-chloro-6-ethoxycaprophenone O-(2-aminoethyl)oxime hydrochloride 10 mmol (2.9 gr) of 4'-amino-6-ethoxycaprophenone O-(2-aminoethyl)oxime were suspended in 10 ml of 6 N HCl, heated for a moment to form a partial solution and then cooled to 0° C. The suspension was then diazotized at 0° C with a solution of 10 mmol (0.7 gr) of $NaNO_2$ in 4 ml of water. After leaving to stand at 0° C for 1 hour the solution was added to a suspension of 11 mmol (1 : 1 gr) of cuprochloride in 10 ml of water of 75° C.

The assembly was then cooled to room temperature and 10 ml of concentrated HCl were added. The suspension was then stirred for another 2 hours and after cooling to 0° C, 20 ml of 50% sodium hydroxide solution were added.

Three extractions with ether were then carried out and the said extract was washed with a 5% sodium bicarbonate solution (1x) and water (1x). The ether was distilled off in vacuo and the residue was purified chromatographically over silica gel with ethanol/ammonia (95 : 5) as an eluent. The solvents were distilled off in vacuo and of the resulting residue the hydrochloride was made in a manner analogous to Example 11c.

After crystallisation from ether/petroleum ether the title compound having a melting point of 63°-66° C was obtained.

(20) 4'-chloro-6-methoxycaprophenone O-(2-aminoethyl) oxime hydrochloride

The title compound having a melting point of 71.5°-73.5° C was obtained in an identical manner from 4'-amino-6-methoxycaprophenone O-(2-aminoethyl) oxime.

(21) 4'-bromo-5-(2-methoxyethoxy)valerophenone O-(2-aminoethyl) oxime fumarate (1 : 1)

In an identical manner the free base of the title compound was made from 4'-amino-5-(2-methoxyethoxy) valerophenone O-(2-amino-ethyl)oxime and was then converted into the fumarate according to example 8. Melting point 142.5°-143.5° C.

(22) 4'-chloro-5-ethoxyvalerophenone O-(2-aminoethyl) oxime fumarate (1 : 1)

24.7 mmol (1.00 ml) of methanol in 3 ml of tetrahydrofuran (THF) were added within 3 minutes to 7.8 mmol (0.3 gr) of $LiAlH_4$ in 10 ml while stirring and cooling in ice water of THF. A solution of 1.15 mmol (0.34 gr) of 4'-chloro-5-ethoxyvalerophenone O-(cyanomethyl) oxime was then added while stirring and cooling within 10 minutes. After stirring the reaction mixture for another 3 hours at 5° C, it was decomposed with 1.0 ml of water. The hydroxides formed were sucked off, washed with chloroform and the filtrate was evaporated to dryness in vacuo. The resulting base was converted into the title compound according to Example 8 which after recrystallisation from alcohol/acetonitrile (1 : 1) had a melting point of 150°-152° C.

(23) Tablet 50 mg of 4'-chloro-5-ethoxyvalerophenone O-(2-aminoethyl) oxime. HCl
335 mg of lactose
60 mg of potato starch
25 mg of talcum
5 mg of magnesium stearate
5 mg of gelatin

(24) Suppository 50 mg of 4'-chloro-5-(2-methoxyethoxy) valerophenone O-(2-aminoethyl) oxime. HCl
1500 mg of suppository mass.

(25) Injection liquid 25 gr of 4'-chloro-6-methoxycaprophenone O-(2-aminoethyl) oxime. HCl
1.80 gr of methyl p-hydroxybenzoate
0.20 gr of propyl p-hydroxybenzoate
9.0gr of sodium chloride
4.0gr of poly(oxyethylene)$_{20}$ sorbitan mono-oleate water to 1000 ml.

What is claimed is:

1. Compounds of the formula

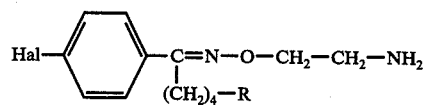

and salts thereof formed with pharmaceutically acceptable acids, in which formula R is an ethoxy-, methoxymethyl-, ethoxymethyl-, methoxyethoxy, cyano- or cyanomethyl group when Hal is a chlorine atom, and R is a cyano-, methoxy- or methoxy-ethoxy group when Hal is a bromine atom.

2. Compounds of the formula

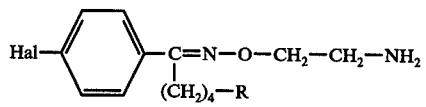

and salts thereof formed with pharmaceutically acceptable acids, in which formula Hal is bromine or chlorine, R is ethoxy-, methoxymethyl-, ethoxymethyl- or methoxyethoxy, when Hal is chlorine, and R is methoxy- or methoxyethoxy when Hal is a bromine atom.

3. The compound 4'-chloro-5-ethoxyvalerophenone O-(2aminoethyl) oxime and its salts with pharmaceutically acceptable acids of claim 2.

4. The compound 4'-chloro-5-(2-methoxyethoxy)-valerophenone O-(2-aminoethyl) oxime and its salts with pharmaceutically acceptable acids of claim 2.

5. The compound 4'-chloro-6-methoxycaprophenone O-(2-aminoethyl) oxime and its salts with pharmaceutically acceptable acids of claim 2.

6. The compound 4'-chloro-6-ethoxycaprophenone O-(2-aminoethyl) oxime and its salts with pharmaceutically acceptable acids of claim 2.

7. The compound 4'-bromo-5-(2-methoxyethoxy)-valerophenone O-(2-aminoethyl) oxime and its salts with pharmaceutically acceptable acids of claim 2.

8. The compound 4'-bromo-5-methoxyvalerophenone O-(2-aminoethyl) oxime and its salts with pharmaceutically acceptable acids of claim 2.

9. 4'-chloro-6-cyanocaprophenone O-(2-aminoethyl) oxime and its salts with pharmaceutically acceptable acids.

10. 4'-chloro-5-cyanovalerophenone O-(2-aminoethyl)oxime and its salts with pharmaceutically acceptable acids.

11. 4'-bromo-5-cyanovalerophenone O-(2-aminoethyl)oxime and its salts with pharmaceutically acceptable acids.

12. A pharmaceutical composition comprising an antidepressively effective amount of a compound of the formula

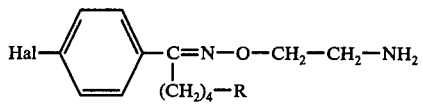

wherein R and Hal are defined as in claim 1 or a salt thereof formed with a pharmaceutically acceptable acid and a pharmaceutically acceptable carrier therefor.

13. A method of treating medically depressed patients comprising administering to said patients an antidepressively effective dosage of the composition of claim 12.

* * * * *